(12) United States Patent
Foley et al.

(10) Patent No.: US 8,100,917 B2
(45) Date of Patent: *Jan. 24, 2012

(54) METHODS AND INSTRUMENTATION FOR DISTRACTION OF A DISC SPACE

(75) Inventors: Kevin T. Foley, Germantown, TN (US); Mingyan Liu, Bourg-la-Reine (FR)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/655,373

(22) Filed: Dec. 30, 2009

(65) Prior Publication Data

US 2010/0241127 A1 Sep. 23, 2010

Related U.S. Application Data

(60) Continuation of application No. 11/028,983, filed on Jan. 4, 2005, now Pat. No. 7,648,512, which is a division of application No. 10/256,338, filed on Sep. 27, 2002, now Pat. No. 6,855,148, which is a division of application No. 09/421,709, filed on Oct. 20, 1999, now Pat. No. 6,500,180.

(51) Int. Cl.
  *A61B 17/58* (2006.01)
(52) U.S. Cl. ...................................................... 606/105
(58) Field of Classification Search .............. 606/99, 606/105; 600/206, 210, 211, 237, 238
See application file for complete search history.

(56) References Cited

U.S. PATENT DOCUMENTS

| | | |
|---|---|---|
| 2,641,833 A | 6/1953 | Need |
| 2,695,607 A | 11/1954 | Hipps et al. |
| 3,998,217 A | 12/1976 | Trumbull et al. |
| 4,545,374 A | 10/1985 | Jacobson |
| 4,573,448 A | 3/1986 | Kambin |
| 4,610,243 A | 9/1986 | Ray |
| 4,899,729 A | 2/1990 | Gill et al. |
| 5,195,541 A | 3/1993 | Obenchain |
| 5,334,194 A | 8/1994 | Mikhail |
| 5,380,331 A | 1/1995 | Mikhail |
| 5,395,317 A | 3/1995 | Kambin |
| 5,431,658 A | 7/1995 | Moskovich |
| 5,439,464 A | 8/1995 | Shapiro |
| 5,512,038 A | 4/1996 | O'Neal et al. |
| 5,571,109 A | 11/1996 | Bertagnoli |
| 5,772,661 A | 6/1998 | Michelson |

(Continued)

FOREIGN PATENT DOCUMENTS

WO  WO 94/28824  12/1994

(Continued)

OTHER PUBLICATIONS

Laparoscopic Bone Dowel Surgical Instruments, Brochure, Sofamor Danek, 1995.

(Continued)

*Primary Examiner* — Nicholas Woodall

(57) ABSTRACT

Methods and instrumentation for surgical procedures relating to preparation of vertebral bodies and a disc space for insertion of spinal implants is disclosed. One instrument is a shim having a blade and a shaft having a first end connected with the blade. The blade is inserted into a distracted disc space to maintain distraction during subsequent procedures. Another instrument is a driver for driving the blade of the shim into the distracted disc space. Various methods contemplate the use of these instruments to maintain disc space distraction during disc space preparation for receiving an implant.

16 Claims, 6 Drawing Sheets

U.S. PATENT DOCUMENTS

| | | | |
|---|---|---|---|
| 5,803,904 | A | 9/1998 | Mehdizadeh |
| 5,899,907 | A | 5/1999 | Johnson |
| 5,899,908 | A | 5/1999 | Kuslich et al. |
| 5,913,860 | A | 6/1999 | Scholl |
| 5,968,098 | A | 10/1999 | Winslow |
| 5,984,967 | A | 11/1999 | Zdeblick et al. |
| 6,010,508 | A | 1/2000 | Bradley |
| 6,030,390 | A | 2/2000 | Mehdizadeh |
| 6,042,582 | A | 3/2000 | Ray |
| 6,059,790 | A | 5/2000 | Sand et al. |
| 6,063,088 | A | 5/2000 | Winslow |
| 6,083,225 | A | 7/2000 | Winslow et al. |
| 6,086,595 | A | 7/2000 | Yonemura et al. |
| 6,113,602 | A | 9/2000 | Sand |
| 6,120,506 | A | 9/2000 | Kohrs et al. |
| 6,156,040 | A | 12/2000 | Yonemura et al. |
| 6,224,607 | B1 | 5/2001 | Michelson |
| 6,500,180 | B1 | 12/2002 | Foley et al. |
| 6,575,899 | B1 | 6/2003 | Foley et al. |
| 6,589,247 | B2 | 7/2003 | McGahan et al. |
| 6,855,148 | B2 | 2/2005 | Foley et al. |
| 2001/0016776 | A1 | 8/2001 | Zuckerman et al. |
| 2003/0199871 | A1 | 10/2003 | Foley et al. |
| 2005/0154396 | A1 | 7/2005 | Foley et al. |

FOREIGN PATENT DOCUMENTS

| | | |
|---|---|---|
| WO | WO 96/27321 | 9/1996 |
| WO | WO 96/27345 | 9/1996 |
| WO | WO 97/23536 | 9/1997 |
| WO | WO 98/04202 | 2/1998 |
| WO | WO 99/09896 | 3/1999 |
| WO | WO 00/44320 | 8/2000 |

OTHER PUBLICATIONS

Surgical Technique Using Bone Dowel Instrumentation for Posterior Approach, Sofamor Danek, 1996.

Anterior Instrumentation Surgical Technique, Sofamor Danek, Copyright 1999.

Posterior Instrumentation Surgical Technique, Sofamor Danek, Copyright 1999.

Reduced Profile Instrumentation Surgical Technique, Sofamor Danek, Copyright 1999.

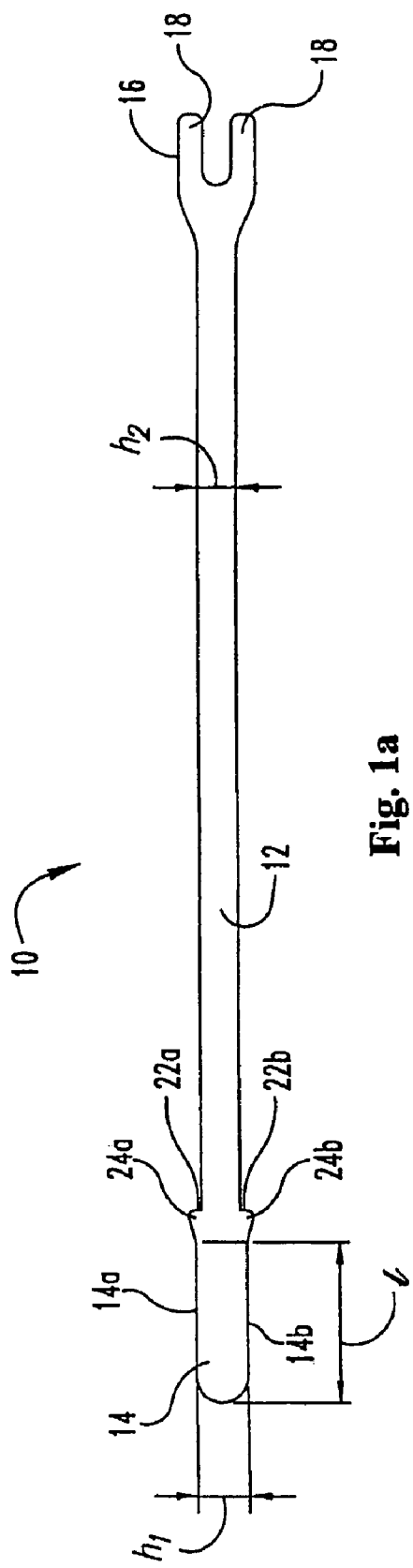
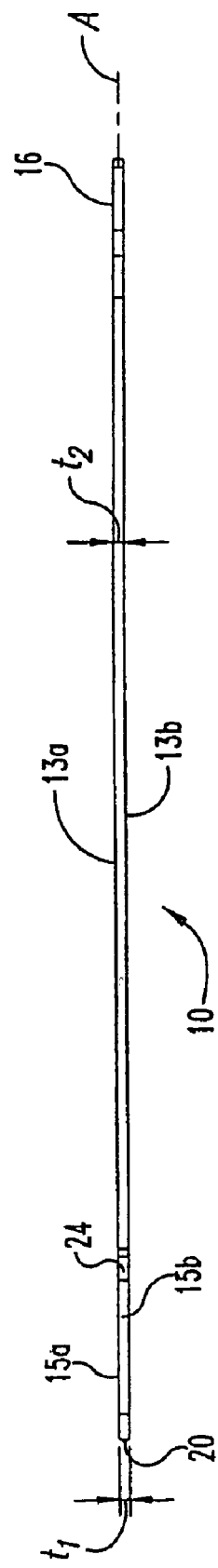

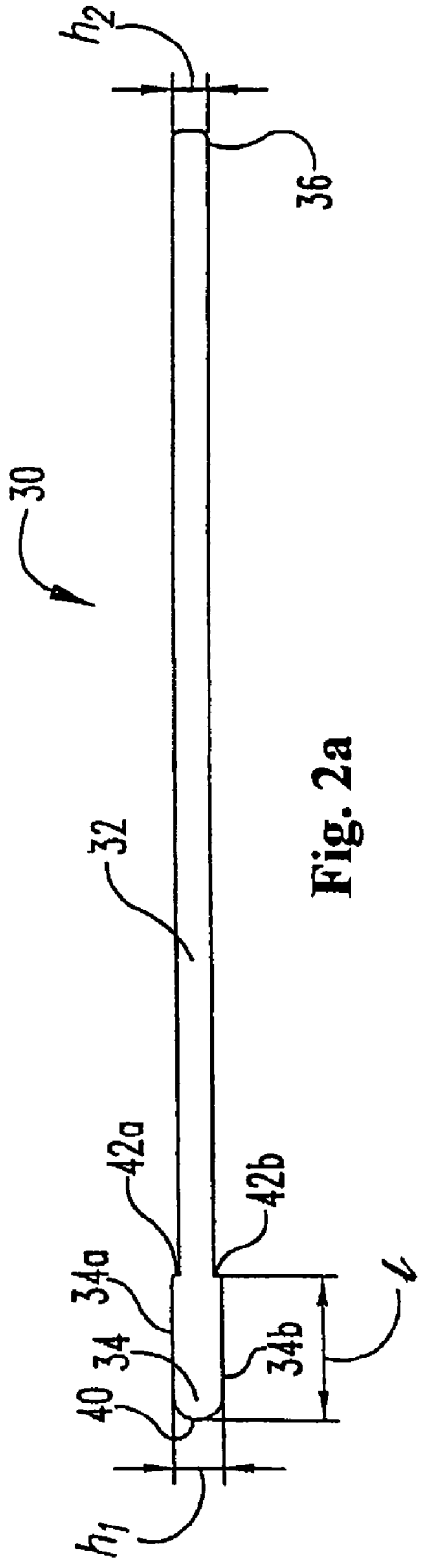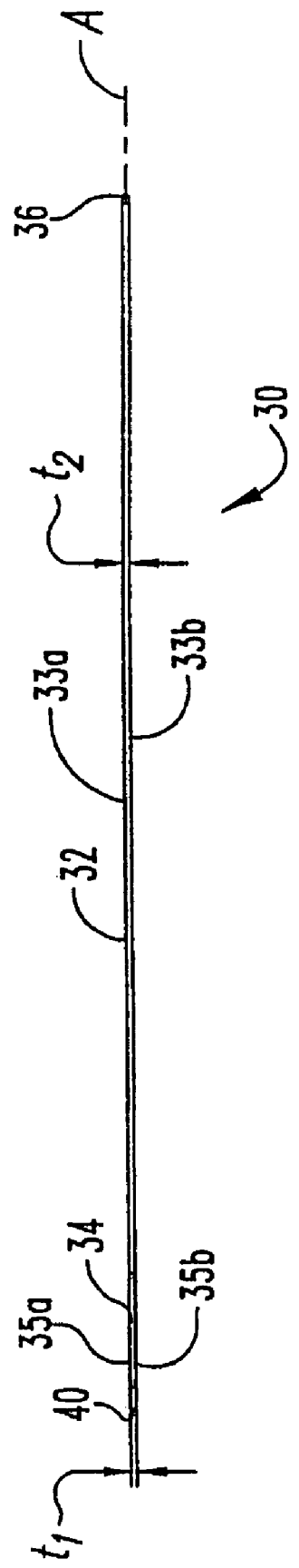
Fig. 2a
Fig. 2b

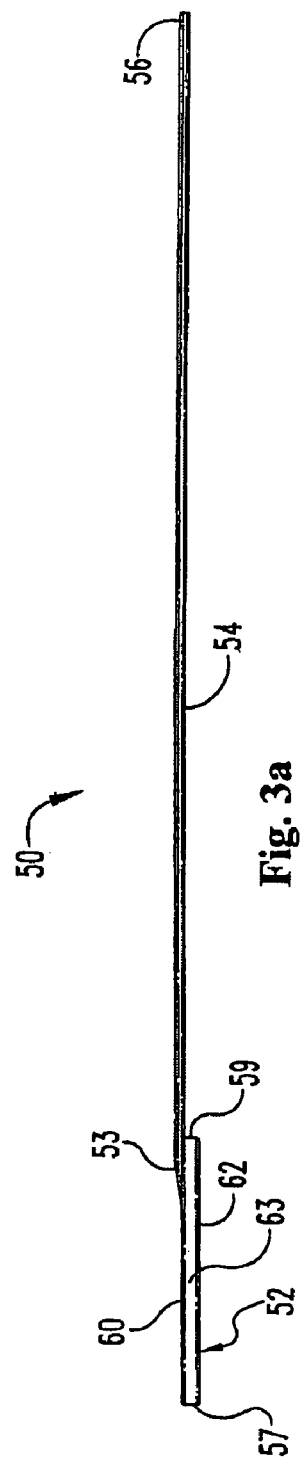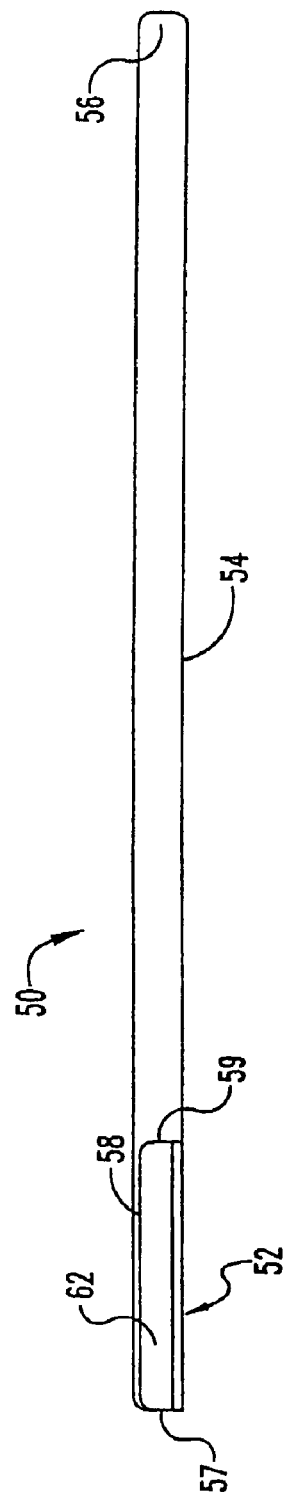
Fig. 3a
Fig. 3b
Fig. 3c

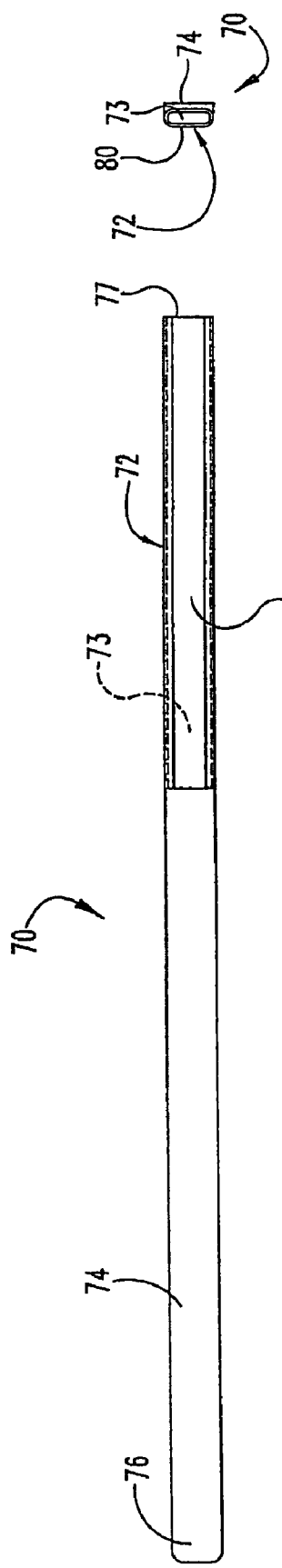
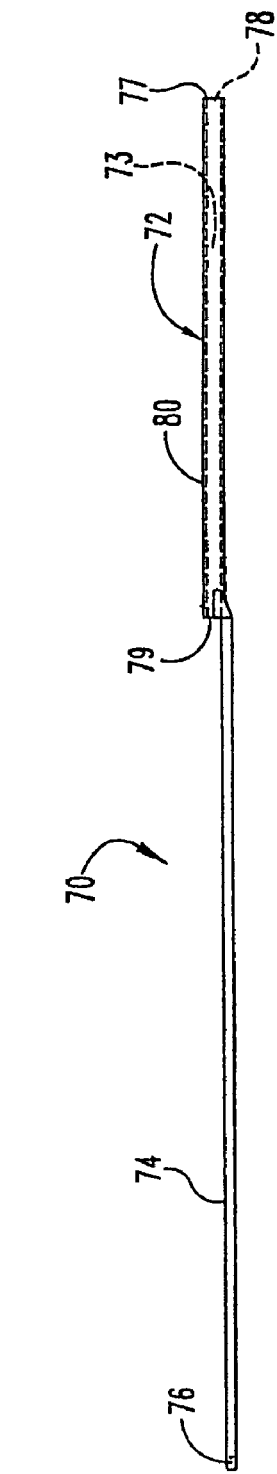
Fig. 4a
Fig. 4b
Fig. 4c

METHODS AND INSTRUMENTATION FOR DISTRACTION OF A DISC SPACE

CROSS-REFERENCE TO RELATED APPLICATIONS

This application is a continuation of U.S. patent application Ser. No. 11/028,983 filed on Jan. 4, 2005, now U.S. Pat. No. 7,648,512 which is a divisional of U.S. patent application Ser. No. 10/256,338, filed on Sep. 27, 2002, now issued as U.S. Pat. No. 6,855,148, which is a divisional of U.S. patent application Ser. No. 09/421,709 filed on Oct. 20, 1999, now issued as U.S. Pat. No. 6,500,180, each of which is incorporated herein by reference in its entirety.

BACKGROUND OF THE INVENTION

The present invention relates generally to surgical procedures for spinal stabilization and more specifically to instrumentation and techniques for preparing an intervertebral disc space for insertion of a spinal implant between adjacent vertebra.

Various surgical methods have been devised for the implantation of fusion devices into the disc space. These methods include anterior, lateral, postero-lateral and posterior approaches to the subject disc space. Many traditional surgical procedures for correction of disc space pathologies can cause significant trauma to the intervening tissues. These open procedures often require a long incision, extensive muscle stripping, prolonged retraction of tissues, denervation and devascularization of tissue. Most of these surgeries require room time of several hours and several weeks of post-operative recovery time due to the use of general anesthesia and the destruction of tissue during the surgical procedure. In some cases, these invasive procedures lead to permanent scarring and pain that can be more severe than the pain leading to the surgical intervention. Instruments that can be used in open procedures that minimize disruption to tissue and nerves surrounding the disc space, yet provide safe and effective disc space preparation during the open procedure would thus be desirable.

Minimally invasive surgical techniques are particularly desirable for spinal and neurosurgical applications because of the need for access to locations deep within the body and the danger of damage to vital intervening tissues. The development of percutaneous spinal procedures has yielded a major improvement in reducing recovery time and post-operative pain because they require minimal, if any, muscle dissection and they can be performed under local anesthesia. One drawback associated with minimally invasive procedures is the relatively small amount of working space available to the surgeon adjacent the cannula or sleeve providing access to the surgical site.

What is therefore needed is instruments and techniques that provide for safe and effective disc space preparation and implant insertion while minimizing trauma to tissue surrounding the surgical site. While the more recent techniques and instrumentation represent an advance over earlier surgical procedures for the preparation of the disc space for insertion of spinal implants, the need for improvement still remains. The present invention is directed to these needs, among others, and provides convenient methods and instruments for use in preparing a disc space for placement of an implant therein.

SUMMARY OF THE INVENTION

One aspect of the present invention is to provide a shim with a thin blade to provide and maintain bi-lateral distraction of a disc space during disc space preparation. The shim comprises a blade and a shaft having a first end connected to the blade and an opposite second end.

Another aspect of the present invention provides a shim that maintains disc space distraction during subsequent spinal procedures for insertion of a spinal implant. The shim includes a blade and a shaft having a first end connected with the blade. The blade has a length extending between a leading end and a trailing end, a height extending between a top and bottom surface, and a width between a first side and a second side of the blade. In one embodiment, the blade has a height to thickness ratio that is greater than 3. In another embodiment, the leading end of the blade is rounded. In yet another embodiment, the trailing end of the blade has a pair of shoulders at the connection with the shaft. In still a further embodiment, the shaft is bendable and has a second end that is configured for connection to an arm engaged to a surgical table. In yet another embodiment, the shim is used in an endoscopically assisted approach and the shaft has a sufficient length to extend through a cannula.

Still a further aspect to the present invention is to provide a spinal disc space shim assembly. The shim assembly includes a shim and a driver for driving the shim into the distracted disc space. The shim includes a blade and a shaft having a first end connected to the blade. A shoulder is formed at the connection between the blade and the shaft. The driver includes a channel at its distal end slidably disposed about the shaft of the shim. The channel has a driving end that impacts the shoulder as the driver is manipulated to impact the shim and drive the blade to a desired depth in the disc space.

In another aspect of the present invention, a method for maintaining disc space distraction during disc space preparation via posterior access to the spine is provided. The method comprising exposing a portion of the dura and retracting the dura and tissue to expose underlying spinal elements. A disc space distractor is inserted on the side of the disc space to distract the disc space to the desire height. A shim having a blade connected to a shaft is inserted on the side of the disc space distractor opposite the nerve root retractor. The blade is sized to maintain the distraction height of the disc space. The disc space distractor is then removed and procedures for preparing the disc space for implant insertion are completed between the nerve root retractor and the disc distractor. In another embodiment, the shim is also inserted on the side of the retractor holding the dura to maintain parallel disc space distraction.

According to another aspect of the invention a method for maintaining disc space distraction is provided. The method includes exposing a portion of the spine at the disc space and bi-laterally distracting the disc space to a desired height with a pair of bi-lateral disc distractors. A first shim is selected that includes a shaft connected to a blade, the blade having a height between a top surface and a bottom surface that corresponds to the distracted disc space height and a thickness between a first side surface and a second side surface. The first shim is inserted into the disc space with one of the side surfaces positioned along one of the pair of bi-lateral disc distractors. The first disc distractor is then removed from the disc space. A second shim is selected that includes a shaft connected with a blade. The blade has a height between a top surface and a bottom surface that corresponds to the distracted disc space height and a thickness between a first side surface and a second side surface. The second shim is inserted into the disc space with one side surface along the other of the pair of bi-lateral disc distractors. The second disc distractor is removed from the disc space and subsequent procedures performed in the distracted disc space between the first and second shims.

The present invention also contemplates a method of preparing a disc space and inserting an implant. The method utilizes one or more of the instruments described above to prepare the disc space for receiving an implant.

Related objects and advantages of the present invention will be apparent from the following description.

BRIEF DESCRIPTION OF THE DRAWINGS

FIG. 1(a) is a top elevational view of a shim according to the present invention.

FIG. 1(b) is a side elevational view of the shim of FIG. 1(a).

FIG. 2(a) is a top elevational view of another embodiment shim according to the present invention.

FIG. 2(b) is a side view of the shim of FIG. 2(a).

FIG. 3(a) is a top elevational view of a driver according to another aspect of the present invention.

FIG. 3(b) is a side elevational view of the driver of FIG. 3(a).

FIG. 3(c) is an end elevational view of the driver of FIG. 3(a).

FIG. 4(a) is a top elevational view of another embodiment driver according to the present invention.

FIG. 4(b) is a side elevational view of the driver of FIG. 4(a).

FIG. 4(c) is an end elevational view of the driver of FIG. 4(a).

DESCRIPTION OF THE PREFERRED EMBODIMENTS

Figure 7:
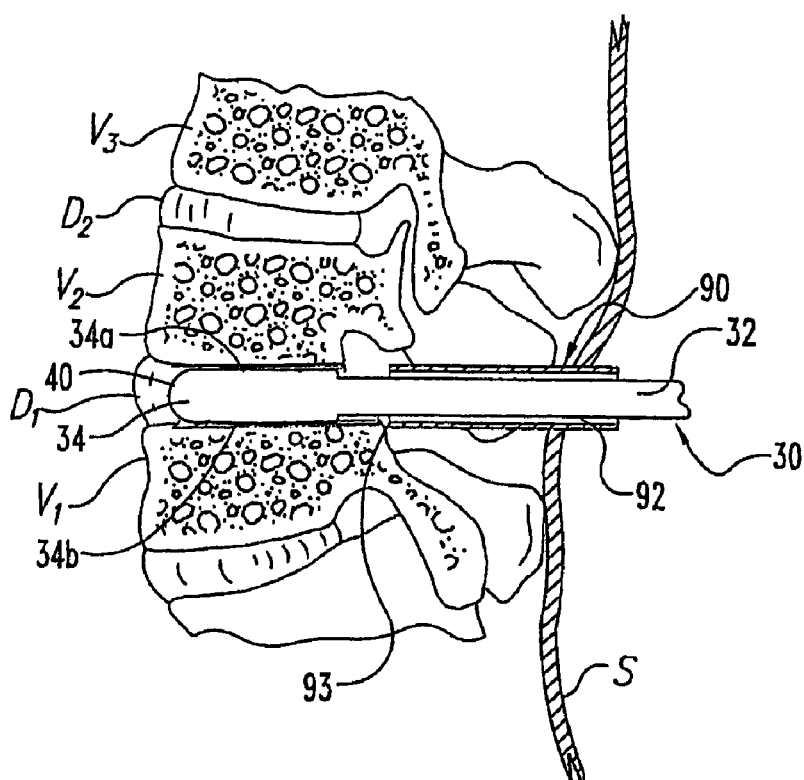
FIG. 7 is a side elevational view of the shim of FIG. 2(a) inserted through a cannula and into the disc space between adjacent vertebrae.

For the purposes of promoting an understanding of the principles of the invention, reference will now be made to the embodiments illustrated in the drawings and specific language will be used to describe the same. It will nevertheless be understood that no limitation of the scope of the invention is thereby intended, such alterations and further modifications in the illustrated devices, and such further applications of the principles of the invention as illustrated therein being contemplated as would normally occur to one skilled in the art to which the invention relates.

The present invention relates generally to instruments and methods for preparing a disc space for insertion of a spinal implant in the disc space. While it should be understood that the instruments disclosed herein have many uses, it is contemplated that they may be used to perform spinal surgical procedures from generally anterior, posterior, postero-lateral, and transforaminal approaches to the spine. The instruments have application in procedures for the cervical, lumbar and thoracic regions of the spine. Such procedures utilizing the instruments of the present invention typically involve, but are not limited to, preparation of the disc space and vertebral bodies for insertion of spinal implants or other devices.

Referring now to FIGS. 1(a) and 1(b), there is shown a shim according to one aspect of the present invention. Shim 10 includes a shaft 12 connected to a blade 14. Blade 14 has a first side surface 15a and a second side surface 15b. While blade 14 is shown as a flat blade, it is contemplated that any of a variety of blade shapes may be utilized in conjunction with shaft 12 of the present invention. A proximal end 16 of shaft 12 includes a pair of prongs 18 defining a slot 19 therebetween. Shaft 12 has opposite flat side surfaces 13a and 13b along the length of shaft 12. Side surfaces 13a and 13b are co-planar with side surfaces 15a and 15b, respectively, of blade 14 and extend generally parallel to axis A. Shaft 12 is bendable in either direction away from a plane that extends through axis A and parallel to side surfaces 13a and 13b. This allows shaft 12 to be bent as needed by the surgeon away from the surgical site. Shaft 12 can be bent for engagement to a surgical table supporting the patient. Prongs 19 are configured for attachment to the table-based arm. Other configurations for the proximal end of shaft 12 that allow attachment of shim 10 to a table-based arm are also contemplated as would occur to those skilled in the art.

Blade 14 has top surface 14a for contacting the superior vertebral endplate in the disc space and bottom surface 14b for contacting the inferior vertebral endplate in the disc space. Blade 14 has a leading end 20 extending between top surface 14a and bottom surface 14b. Preferably, leading end 20 is rounded to facilitate insertion of blade 14 into the disc space. Blade 14 also includes a pair of shoulders 22a and 22b. One shoulder 22a extends between shaft 12 and top surface 14a, and the other shoulder 22b extends between shaft 12 and bottom surface 14b. In one embodiment, shoulders 22a and 22b include flanges 24a and 24b, respectively, extending above top surface 14a and bottom surface 14b. Preferably, flanges 24a and 24b are rounded, and function as a depth stop to resist insertion of blade 14 into the disc space when the flanges 24a and 24b contact the vertebral bodies. When blade 14 is inserted into the disc space, first side surface 15a and second side surface 15b protect the disc space and prevent migration of tissue and other anatomical material laterally into the disc space during subsequent surgical procedures.

Blade 14 as a length l extending between leading end 20 and flanges 24. Preferably, length l is selected based on the depth of the disc space and the desired insertion depth of blade 14. Blade 14 also has a height h1 between top surface 14a and bottom surface 14b. Height h1 is preferably selected based on the height of the disc space between the endplates of the adjacent vertebrae after the disc space has been finally distracted. Blade 14 has a thickness t2 measured between first side surface 15a and second side surface 15b. In one form, it is contemplated that ratio of height h1 to thickness t1 is more than about 3.0. In another preferred form, this ratio is greater than about 5.0. Shaft 12 has a height h2, and a thickness t2 that is the same as thickness t1. However, it is also contemplated herein that thickness t1 and t2 can have different values and that side surface 13a and/or 13b are not co-planar with side surface 15a and 15b of blade 14, but rather extend in parallel planes. It is preferred that height h1 of blade 14 is greater than height h2 of shaft 12.

Referring now to FIGS. 2(a)-2(b), another embodiment of the shim of the present invention is shown. Shim 30 includes a shaft 32 connected to a blade 34. Blade 34 has a first side surface 35a and a second side surface 35b. While blade 34 is shown as a flat blade, it is contemplated that any of a variety of blade shapes may be utilized in conjunction with shaft 32 of the present invention. Shaft 32 extends to proximal end 36.

Shaft 32 has opposite flat side surfaces 33a and 33b along the length of shaft 32. Side surfaces 33a and 33b are co-planar with side surfaces 35a and 35b, respectively, of blade 34 and extend generally parallel to axis A. Shaft 32 is bendable in either direction away from a plane that extends through axis A and parallel to side surfaces 33a and 33b. This allows shaft 32 to be bent as needed by the surgeon away from the surgical site.

Blade 34 has top surface 34a for contacting the superior vertebral endplate in the disc space and bottom surface 34b for contacting the inferior vertebral endplate in the disc space. Blade 34 has a leading end 40 extending between top surface 34a and bottom surface 34b. Preferably, leading end 40 is rounded to facilitate insertion of blade 34 into the disc space. Blade 34 also includes a pair of shoulders 42a and 42b. One shoulder 42a extends between shaft 32 and top surface 34a, and the other shoulder 42b extends between shaft 32 and bottom surface 34b. When blade 34 is inserted into the disc space, side surfaces 35a, 35b protect the disc space and prevent migration of tissue and other anatomical material laterally into the disc space during subsequent surgical procedures.

Blade 34 has a length l extending between leading end 40 and shoulders 42a, 42b. Preferably, length l is selected based on the depth of the disc space and the desired insertion depth of blade 34. Blade 34 also has a height h1 between top surface 34a and bottom surface 34b. Height h1 is preferably selected based on the height of the distracted disc space after it has been finally distracted. Blade 34 has a thickness t2 measured between first side surface 35a and second side surface 35b. As with the embodiment of FIGS. 1(a) and 1(b), it is contemplated that ratio of height h1 to thickness t1 is greater than about 3.0. In a most preferred form, this ratio is greater than about 5.0. Shaft 32 has a height h2, and a thickness t2 that is the same as blade thickness t1. However, it is also contemplated herein that thickness t1 and t2 have different values and that side surface 33a and/or 33b are not co-planar with side surface 35a and 35b of blade 34, but rather extend in parallel planes. It is preferred that height h1 of blade 34 is greater than height h2 of shaft 32.

In a specific embodiment of shims 10 and 30, blade 14, 34 have thickness t1 of about 1.5 millimeters. Height h1 for the smallest sized blade 14, 34 is 8.0 millimeters, and additional larger heights h1 are provided in increments of 2 millimeters. The shafts 12, 32 in this specific embodiment have a height h2 of 6.0 millimeters and a thickness t2 of about 1.5 millimeters. Shims 10, 30 are preferably fabricated from aluminum, but other materials, such as other metal materials or plastic, are also contemplated herein as would occur to those skilled in the art.

Referring now to FIGS. 3(a)-3(c), a driver 50 for impacting or driving the shim 10 or 30 into the disc space is provided. Driver 50 includes a channel 52 and a handle 54 extending between a distal end 53 and a proximal end 56. Channel 52 is connected to distal end 53 of handle 54 and extends distally therefrom. Driver 50 is particularly suited for the shim 10 because it allows side-loading of the shaft 12 into channel 52. Preferably, channel 52 is offset from handle 54, as shown in FIG. 3(b), to facilitate insertion of shafts 12, 32 into channel 52 and manipulation of driver 50 with respect to shim 10, 30.

Channel 52 has a first wall 60 and a second wall 62 connected by radius 64. Channel 52 has opening 58 opposite radius 64 communicating with receptacle 63 between first wall 60 and second wall 62. Receptacle 63 extends along the length of channel 52 and is open at each end of channel 52. Receptacle 63 is sized to slidably receive shaft 12 of shim 10 therein or the shaft 32 of shim 30. Channel 52 includes a driving end 57. Channel 52 is configured so that driving end 57 contacts shoulders 22a, 22b of shim 10 or shoulders 42a, 42b of shim 30.

Use of driver 50 will now be described with respect to shim 10, it being understood that shim 30 may also be used with driver 50. Blade 14 is positioned at the desired lateral insertion location adjacent the distracted disc space. The channel 52 is then side-loaded onto shaft 12 and then positioned adjacent the blade 14. It is contemplated that a driving force can be provided to insert blade 14 into the disc space by withdrawing driver 50 a short distance away from shoulders 22a, 22b, and then applying a downward force so that driving end 57 impacts the shoulders 22a, 22b. This process is repeated until flanges 24a, 24 contact the adjacent vertebral bodies and resist further insertion of blade 14 into the disc space. It is also contemplated that the driving force may be applied through driver 50 via a hammer, mallet or other device impacting the driver 50. Driver 50 delivers the driving force directly to blade 14 without impacting shaft 12.

Referring now to FIGS. 4(a)-4(c), a driver 70 for impacting or driving the shim 30 into the disc space is provided. Driver 70 includes a channel 72 and a handle 74 extending between a distal end 73 and a proximal end 76. Channel 72 is connected to distal end 73 of handle 74 and extends therefrom. Driver 70 is particularly suited for the shim 30 because channel 72 is end-loaded over proximal end 36 of shaft 32. Preferably, channel 72 is offset from the handle 74, as shown in FIG. 4(b), to facilitate insertion of shaft 32 into channel 72 and manipulation of driver 70 with respect to shim 30.

Channel 72 has a wall 80 that extends therearound. Channel 72 has end openings 78, 79 and a receptacle 73 defined by wall 80 that extends along the length of channel 72. Receptacle 73 is sized to slidably receive shaft 32 of shim 30 therein. Channel 72 includes a driving end 77 configured to contact shoulders 42a, 42b of shim 30. Driver 70 delivers the driving force directly to blade 34 without impacting shaft 32.

Use of driver 70 will now be described with respect to shim 30. Blade 34 is positioned at the desired lateral insertion location adjacent the distracted disc space. The channel 72 is then end-loaded onto shaft 32 by placing opening 78 over proximal end 36. Driver 70 is slid along shaft 32 until driving end 77 is positioned adjacent blade 34. It is contemplated that a driving force can be provided to insert blade 34 into the disc space by withdrawing driver 70 a short distance away from shoulders 42a, 42b, and then applying a downward force so that driving end 77 impacts the shoulders 42a, 42b. This process is repeated until blade 34 is inserted to the desired depth in the disc space. It is also contemplated that the driving force may be applied through driver 70 via a hammer, mallet or other device impacting the driver 70. The depth of insertion can be monitored using x-ray techniques or other techniques that allow visualization of blade 34 in the disc space. Thus, it is preferred that blade 34 be radiolucent. Since shim 30 does not include flanges 24a, 24b, the overall height of the construct is minimized. Further, the elimination of prongs 18 allows end-loading of the driver 70. Thus, shim 30 and driver 70 have particularly useful application in endoscopically assisted, minimally invasive approaches to the spine.

Figure 5:
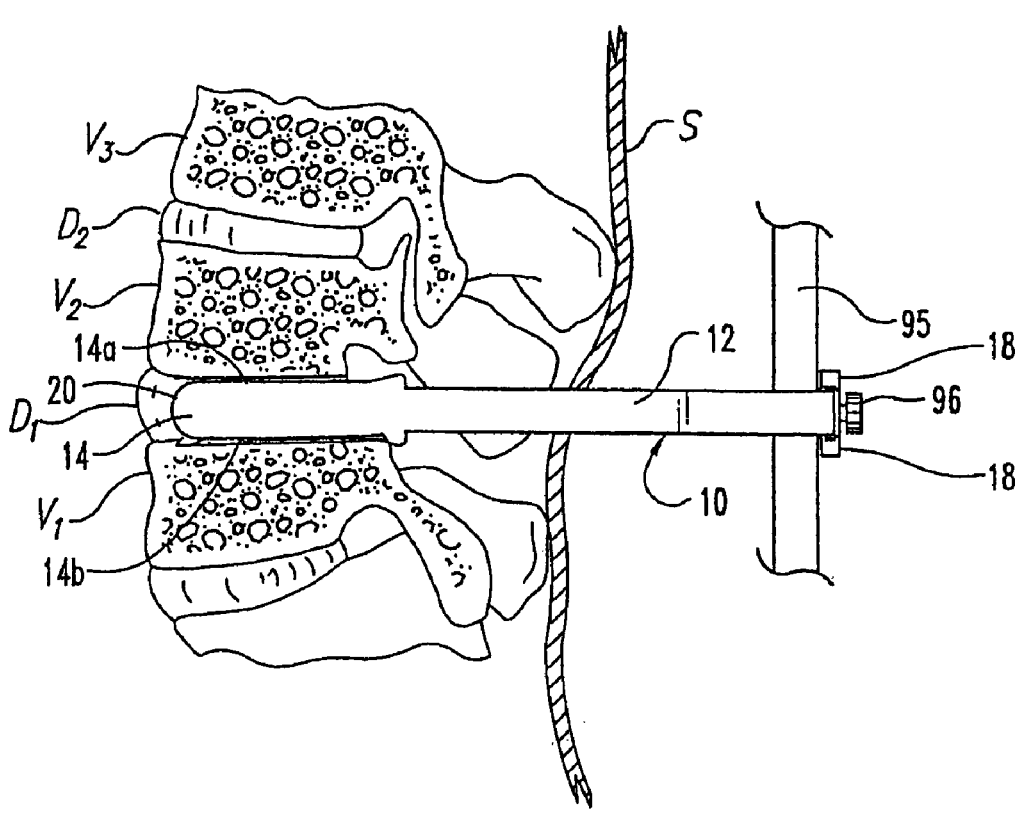
FIG. 5 is a side elevational view of a shim according to FIG. 1(a) inserted into the disc space between two adjacent vertebrae.

In use in an open procedure, an initial incision provides the approach and exposure of the posterior spinal surgical site. Exposure of the dura is accomplished in a customary fashion. A retractor is used to retract the dura. The disc space and vertebrae are then prepared for distraction by performing, for example, an annulotomy. A first distractor is inserted into one side of the disc space. A second distractor is inserted into the other side of the disc space. Various sized distractors may be sequentially inserted to bi-laterally distract the disc space to the desired height. Shim 10 is inserted into the disc space adjacent a first one of the distractors using driver 50. As shown in FIG. 5, the top surface 14a and bottom surface 14b contact the endplates of vertebrae V1 and V2, respectively, in the disc space D1. If appropriate, the shim is connected to a table-based arm 95 via the prongs 18 and fastener 96. The first distractor is then removed. At this point, endplate preparation procedures can be completed in the disc space between the second distractor and the shim 10. However, it is contemplated that a second shim 10 can be inserted adjacent the second distractor. The second distractor is then removed. Discectomy, endplate preparation, or other procedures may then be competed in the disc space between the shims.

Figure 6:
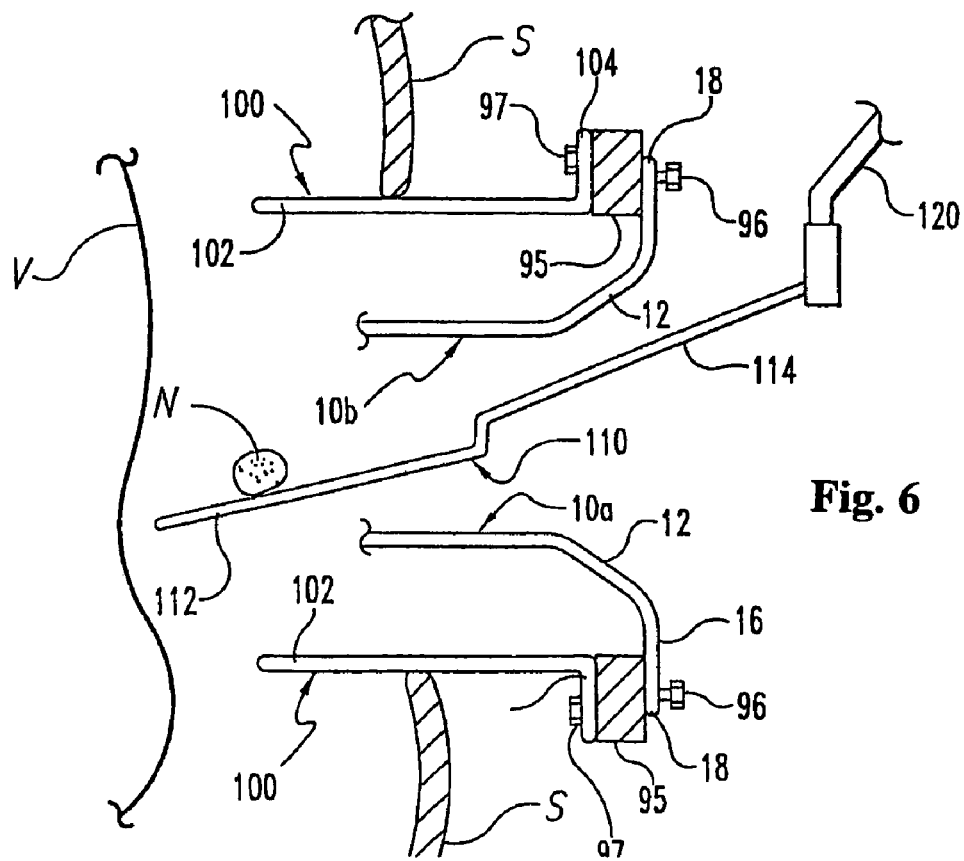
FIG. 6 is a side elevational view of surgical instruments utilized in an open posterior approach to the spine with the shim of FIG. 1(a).

A side view of an open approach to the spine is illustrated in FIG. 6. Skin S is retracted by a pair of retractors 100 connected to table-based arm 95. Retractors 100 have valves 102 extending through the skin S to maintain the open surgical site. Retractors 100 also include extension 104 extending from valve 102 for connection to arm 95 via fastener 97. Dural sac or nerve N is retracted via nerve root retractor 110. Retractor blade 112 is used to maintain the position of nerve N away from the surgical instruments on the working side of retractor 112 and to protect nerve N from instruments used during the procedure. A shaft 114 extends from blade 112, where is connected to a tool 120 that allows the surgeon to manipulate blade 112. After the disc space is distracted as described above, a first one of the shims 10a is inserted and the distractor on the working side of retractor 110 is removed. With the distractor removed, the surgeon can complete surgical procedures between shim 10a and retractor 112 while the parallel disc space distraction is maintained. Also, the surgeon has the option of inserting a second shim 10b into the distracted disc space and removing the second distractor. This increases the space available for nerve N on this side of retractor 112, reducing the risk of pinching of nerve N by the instruments.

The present invention also has application in procedures utilizing a single distractor to distract the disc space. The shims are inserted in the disc space on each side of the single distractor before the distractor is removed to maintain the parallel disc space distraction. In addition, the present invention contemplates procedures that use only a single shim on one side of the distracted disc space. The other side of the distracted disc space is maintained by a distractor, by an already inserted implant, or is simply left unsupported.

The present invention also has application in minimally-invasive surgical procedures that utilize an endoscopically assisted approach, stereotactic imaging, image-guidance technology, and any other type of viewing system used in a minimally invasive approach that would occur to one skilled in the art. Referring now to FIG. 7, a minimally invasive approach utilizes a cannula 90 that is positioned with insertion end 92 adjacent the disc space. Cannula 90 provides the surgeon access to the disc space through a working channel 92 to perform various procedures, including disc space distraction. After the disc space is finally distracted via a distractor, shim 30 is inserted through cannula 90 and into disc space D1 adjacent the distractor between vertebrae V1 and V2 using driver 70. Top surface 34a of blade 34 contacts the end plate of vertebra V2 and bottom surface 34b contacts the end plate of vertebra V1. The distractor may then be removed, and shaft 32 can be bent away from the working channel 92 of cannula 90 and out of the way of the surgeon.

Figure 9:
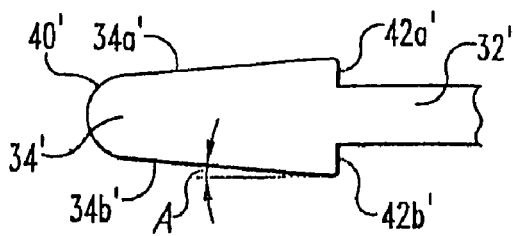
FIG. 9 is a side elevational view of an alternate embodiment blade for the shim of FIG. 2(a).
Figure 8:
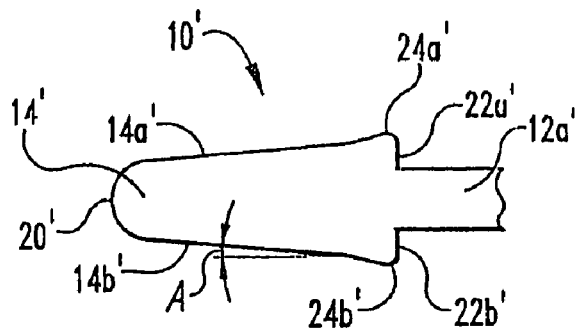
FIG. 8 is a side elevational view of an alternate embodiment blade for the shim of FIG. 1(a).

Alternate embodiments of shims 10 and 30 are illustrated in FIGS. 8 and 9, respectively. Shim 10' of FIG. 8 is similar in every respect to shim 10 of FIG. 1(a) except as to blade 14'. Blade 14' has a top surface 14a' and bottom surface 14b' that converge towards leading end 20'. This convergence is indicated as angle A, and approximates the lordotic curvature of the vertebrae on either side of the disc space in which the shim 10' is to be inserted. Similarly, shim 30' of FIG. 9 is similar in every respect to shim 30 of FIG. 2(a) except as to blade 34'. Blade 34' has a top surface 34a' and bottom surface 34b' that converge towards leading end 40'. This convergence is indicated as angle A, and approximates the lordotic curvature of the vertebrae on either side of the disc space in which the shim 10' is to be inserted.

Utilization of the above-described shims provides several advantages over disc distractors and other techniques for preparing a disc space for implant insertion. The relatively thin blade design provides increased working room in the disc space during procedures completed after insertion of the shims. The shims also enable bi-lateral support of the disc space during disc space preparation procedures, thus maintaining the vertebral endplates in a parallel relationship. Maintenance of the parallel relationship between the endplates allows uniform and precise preparation of the endplates and better control of the procedures performed on the endplates. For example, the amount and depth of endplate material removed at bi-lateral locations in the disc space during a reaming procedure is uniform and more precise if the distracted height and the parallel endplate relationship are maintained throughout the procedure. The shims provide stability to the distracted disc space when connected with a table-based arm. The shims also protect tissue surrounding the disc space and block migration of tissue into the disc space. The shims minimize the obstruction in the operative field normally associated with disc distractors and provides for increased access to the operative site. The shims also enable nerves and other tissue to be retracted while minimizing the risk of pinching the nerves and trauma to the tissue.

While the invention has been illustrated and described in detail in the drawings and foregoing description, the same is to be considered as illustrative and not restrictive in character, it being understood that only the preferred embodiments have been shown and described and that all changes and modifications that come within the spirit of the invention are desired to be protected.

What is claimed is:

1. An instrument for spinal disc space distraction, comprising:
   a blade having a length extending between a leading end and a trailing end, a height extending between a top surface and a bottom surface, and a thickness extending between a first side surface and a second side surface, wherein said first side surface and said second side surface are substantially parallel to one another and said blade includes a height to thickness ratio greater than 3; and
   a shaft having a first end and an opposite second end and a pair of opposite side surfaces extending therebetween, said first end connected to said trailing end of said blade, said opposite side surfaces of said shaft being substantially parallel to one another and each being co-planar with a respective one of said first and second side surfaces of said blade, wherein said blade includes a pair of shoulders at said trailing end that extend from said shaft to a respective one of said top and bottom surfaces of said blade and said pair of shoulders face said second end of said shaft to receive a driving force that is directed toward said leading end of said blade, wherein said height from said top surface to said bottom surface of said blade at said shoulders is greater than a height of said shaft from one of said opposite sides to the other of said opposite sides at said first end of said shaft where said blade and said shaft are connected.

2. The instrument of claim 1, wherein each of said shoulders includes a flange projecting beyond a respective one of said top and bottom surfaces of said blade.

3. The instrument of claim 1, wherein said shaft is bendable along a length thereof away from a plane through an axis extending parallel to said first and second side surfaces of said blade when said blade is positioned in the distracted disc space.

4. The instrument of claim 1, wherein said second end of said shaft includes a pair of prongs forming a gap therebetween.

5. The shim of claim 1, wherein said top surface and said bottom surface of said blade are parallel to one another in a direction extending from said trailing end toward said leading end.

6. The instrument of claim 1, wherein said top surface and said bottom surface of said blade converge toward one another in a direction extending from said trailing end toward said leading end.

7. The instrument of claim 1, further comprising a cannula with a working channel and said blade and said shaft of said shim are positionable through said working channel.

8. An instrument for spinal disc space distraction, comprising:
 a shaft having a first end a second end and a pair of opposite side surfaces extending therebetween, said opposite side surfaces of said shaft being substantially parallel to one another; and
 a blade connected to said first end of said shaft, said blade having a length extending between a leading end and a trailing end and a top surface and a bottom surface substantially parallel to said top surface and a first side surface and an oppositely facing second side surface that each extend along a major portion of said length of said blade, wherein said first and second side surfaces of said blade are co-planar with respective ones of said opposite side surfaces of said shaft, said blade further including a pair of shoulders at said trailing end of said blade where said blade is connected to said first end of said shaft, said pair of shoulders facing said second end of said shaft to receive a driving force that is directed toward said leading end of said blade, wherein said shoulders extend from opposite sides of said shaft toward a respective one of said top and bottom surfaces of said blade, wherein at said shoulders said height of said blade from said top surface to said bottom surface is greater than a height of said shaft from one of said opposite sides to the other of said opposite sides at said first end of said shaft where said blade and said shaft are connected.

9. The instrument of claim 8, wherein each of said shoulders includes a flange projecting beyond a respective one of said top and bottom surfaces of said blade.

10. The instrument of claim 8, wherein said first and second side surfaces extend from said top surface to said bottom surface of said blade.

11. The instrument of claim 10, wherein said first and second side surfaces of said blade are substantially parallel to one another.

12. The instrument of claim 10, wherein said opposite surfaces of said shaft are flat and said first and second side surface of said blade are flat.

13. The instrument of claim 12, wherein said blade has a height to thickness ratio greater than 3.

14. The instrument of claim 10, wherein said shaft is bendable along a length thereof away from a plane through an axis extending parallel to said first and second side surfaces of said blade when said blade is positioned in the distracted disc space.

15. The instrument of claim 8, wherein said second end of said shaft includes a pair of prongs forming a gap therebetween.

16. The instrument of claim 8, further comprising a cannula with a working channel and said blade and said shaft of said shim are positionable through said working channel.

* * * * *